(12) United States Patent
Nam et al.

(10) Patent No.: US 10,314,709 B2
(45) Date of Patent: Jun. 11, 2019

(54) BONE REGENERATION DEVICE

(71) Applicant: INDUSTRY-ACADEMIC COOPERATION FOUNDATION GYEONGSANG NATIONAL UNIVERSITY, Gyeongsangnam-do (KR)

(72) Inventors: Tae-Hyeon Nam, Gyeongsangnam-do (KR); Ji-Wook Lee, Seoul (KR); Yeon-Wook Kim, Daegu (KR); Gyu-Bong Cho, Gyeongsangnam-do (KR); Jung-Pil Noh, Gyeongsangnam-do (KR)

(73) Assignee: INDUSTRY-ACADEMIC COOPERATION FOUNDATION GYEONGSANG NATIONAL UNIVERSITY, Gyeongsangnam-do (KR)

(*) Notice: Subject to any disclaimer, the term of this patent is extended or adjusted under 35 U.S.C. 154(b) by 0 days.

(21) Appl. No.: 15/504,587

(22) PCT Filed: Nov. 18, 2014

(86) PCT No.: PCT/KR2014/011065
§ 371 (c)(1),
(2) Date: Feb. 16, 2017

(87) PCT Pub. No.: WO2016/080566
PCT Pub. Date: May 26, 2016

(65) Prior Publication Data
US 2017/0245996 A1 Aug. 31, 2017

(30) Foreign Application Priority Data
Nov. 17, 2014 (KR) .................. 10-2014-0160340

(51) Int. Cl.
A61F 2/28 (2006.01)
A61N 2/02 (2006.01)
(Continued)

(52) U.S. Cl.
CPC .............. *A61F 2/28* (2013.01); *A61L 27/047* (2013.01); *A61L 27/12* (2013.01); *A61L 27/50* (2013.01);
(Continued)

(58) Field of Classification Search
CPC ... A61N 1/18; A61N 1/20; A61N 1/32; A61N 2/002; A61L 2430/02; A61F 2002/2821
See application file for complete search history.

(56) References Cited

U.S. PATENT DOCUMENTS 4,602,638 A * 7/1986 Adams .................. A61N 1/05
607/52
6,095,148 A 8/2000 Sharstri et al.
(Continued)

FOREIGN PATENT DOCUMENTS

JP 2000237219 A 9/2000
KR 1019990067321 A 8/1999
(Continued)

OTHER PUBLICATIONS

Ercan et al., The effect of biphasic electrical stimulation on ostoblast function at anodized nanotubular titanium surfaces, Feb. 11, 2010, Biomaterials 31, pp. 3684-3693.*
(Continued)

*Primary Examiner* — Brian A Dukert
(74) *Attorney, Agent, or Firm* — Ohlandt, Greeley, Ruggiero & Perle, L.L.P.

(57) ABSTRACT

Disclosed is a bone regeneration device which forms an electric field on a scaffold inserted into a bone damage site. The present bone regeneration device comprises: a battery;
(Continued)

a first electric conductor to be connected to a first electrode of the battery and inserted into a bone located on one side of the scaffold; and a second electric conductor to be connected to a second electrode of the battery and inserted into a bone located on the other side of the scaffold, wherein the battery forms an electric field on the scaffold by applying voltage to the first electric conductor and the second electric conductor.

8 Claims, 13 Drawing Sheets

(51) Int. Cl.
*A61L 27/56* (2006.01)
*A61L 27/04* (2006.01)
*A61L 27/12* (2006.01)
*A61L 27/54* (2006.01)
*A61N 2/00* (2006.01)
*A61L 27/50* (2006.01)

(52) U.S. Cl.
CPC ............... *A61L 27/54* (2013.01); *A61L 27/56* (2013.01); *A61N 2/002* (2013.01); *A61N 2/02* (2013.01); *A61F 2002/2821* (2013.01); *A61L 2300/102* (2013.01); *A61L 2300/112* (2013.01); *A61L 2430/02* (2013.01)

(56) References Cited

U.S. PATENT DOCUMENTS

| | | | |
|---|---|---|---|
| 6,143,035 A * | 11/2000 | McDowell | A61B 17/68 607/50 |
| 7,840,272 B2 | 11/2010 | Kronberg et al. | |
| 9,101,695 B2 | 8/2015 | Langer et al. | |
| 2003/0125769 A1 | 7/2003 | Brighton | |
| 2010/0241229 A1 | 9/2010 | Baehre et al. | |

FOREIGN PATENT DOCUMENTS

| | | |
|---|---|---|
| KR | 20060021366 A | 3/2006 |
| KR | 100791512 B1 | 1/2008 |
| KR | 20080027325 A | 3/2008 |
| KR | 20090015077 A | 2/2009 |
| KR | 20100068363 A | 6/2010 |
| KR | 20110025327 A | 3/2011 |

OTHER PUBLICATIONS

International Search Report dated Aug. 3, 2015 for PCT application No. PCT/KR2014/011065.
Written Opinion dated Aug. 3, 2015 for PCT application No. PCT/KR2014/011065.
Korean Office Action dated Apr. 20, 2016 for Korean application No. 10-2014-0160340.

* cited by examiner

BONE REGENERATION DEVICE

TECHNICAL FIELD

The present invention relates to a bone regeneration device, and more particularly, to a bone regeneration device which promotes bone cell regeneration by arranging electric conductors coupled to a battery in one side and the other side of a scaffold.

BACKGROUND ART

Scaffolds refer to an artificially created structure for tissue establishment and cell function control. For example, the scaffolds serve as a cell adhesion inducing substance and act as a support that bone cells are proliferated and differentiated.

On the other hand, bones are composed of calcium, phosphorous, minerals, and the like. In response to the bone cell being grown using the scaffold, ions which form the bone cell have to be attached to the scaffold.

However, there was a problem that the ions which form the bon cell move in the body in a regular pattern according to the physiological action and thus the ions are not attached to the scaffold well only through insertion of the scaffold and the bone cell formation is delayed.

DETAILED DESCRIPTION OF THE INVENTION

Technical Problem

The present invention has been made in view of the above problems, and the present invention relates to a bone regeneration device which promotes bone cell regeneration by arranging electric conductors coupled to a battery in one side and the other side of a scaffold.

Technical Solution

To obtain the above-described object, the present invention is to provide a bone regeneration device which forms an electric field on a scaffold inserted into a bone damage site, the bone regeneration device including, a first electric conductor which is coupled to a first electrode of the battery and is to be inserted into a bone located in one side of the scaffold, and a second electric conductor which is coupled to a second electrode of the battery and is to be inserted into a bone located in the other side of the scaffold, wherein the battery forms the electric field on the scaffold by applying voltages to the first electric conductor and the second electric conductor.

The bone regeneration device may further include a support on which the battery is to be mounted and one-end portions of the first electric conductor and the second electric conductor may be coupled to the support and the other-end portions of the first electric conductor and the second electric conductor may be inserted into bones.

The first electric conductor and the second electric conductor may have a plate shape.

The bone regeneration device may further include a switching circuit configured to periodically change polarities of the first electric conductor and the second electric conductor.

The present invention is to provide a bone regeneration device including a scaffold which is inserted into a bone damage site and ions for bone cell regeneration are attached thereto and a battery disposed on the scaffold, wherein a first electrode and a second electrode of the battery are formed in one side and the other side of the scaffold and the battery forms an electric field on the scaffold by applying voltages to the first electrode and the second electrode.

The battery may be attached to the scaffold in a form which surrounds the scaffold.

The battery may have a thread shape.

The bone regeneration device may further include a first electric conductor coupled to the first electrode, a second electric conductor coupled to the second electrode, and a switching circuit configured to periodically change polarities of the first electric conductor and the second electric conductor.

The present invention is to provide a bone regeneration device including a scaffold which is inserted into a bone damage site and ions for bone cell regeneration are attached thereto and a thread-shaped battery surrounding the scaffold, wherein a first electrode and a second electrode of the battery may be electrically coupled to each other and the battery forms a magnetic field on the scaffold through current applied thereto.

Current may flow in an inside of the battery.

MODE FOR INVENTION

Hereinafter, the present invention will be described in detail with reference to accompanying drawings.

Figure 1:
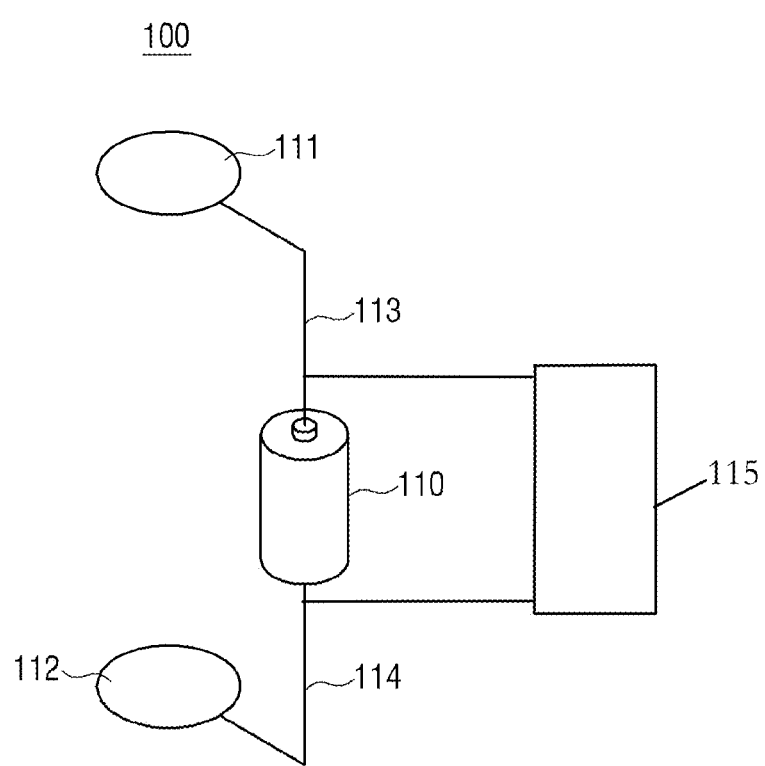
FIG. 1 is a diagram illustrating a bone regeneration device according to an embodiment of the present invention.

FIG. 1 is a diagram illustrating a bone regeneration device according to an embodiment of the present invention.

Referring to FIG. 1, a bone regeneration device 100 includes a battery 110, a first electric conductor 111, a second electric conductor 112, a first electric wiring 113, and a second electric wiring 114.

The bone regeneration device 100 forms an electric field on a scaffold (not shown) inserted into a bone damage site.

The battery 110 may be a device configured to supply power to an external circuit by converting chemical energy to electric energy. The battery 110 may include a secondary battery, but this is not limited thereto.

The first electric conductor 111 may be coupled to a first electrode (anode) of the battery 110 through the first conductive wiring 113. The second electric conductor 112 may be coupled to a second electrode (cathode) of the battery 110 through the second conductive wiring 114. Accordingly, the battery 110 may form an electric field between the first electric conductor 111 and the second electric conductor 112 by applying voltages to both ends of the first electric conductor 111 and the second electric conductor 112.

It has been illustrated in FIG. 1 that the first electric conductor 111 and the second electric conductor 112 have a disc shape, but this is not limited thereto. For example, the first electric conductor 111 and the second electric conductor 112 may have a bone screw shape.

The outside of the battery 110 may be formed of a biocompatible material and may prevent the human body from being harmful.

Figure 2:
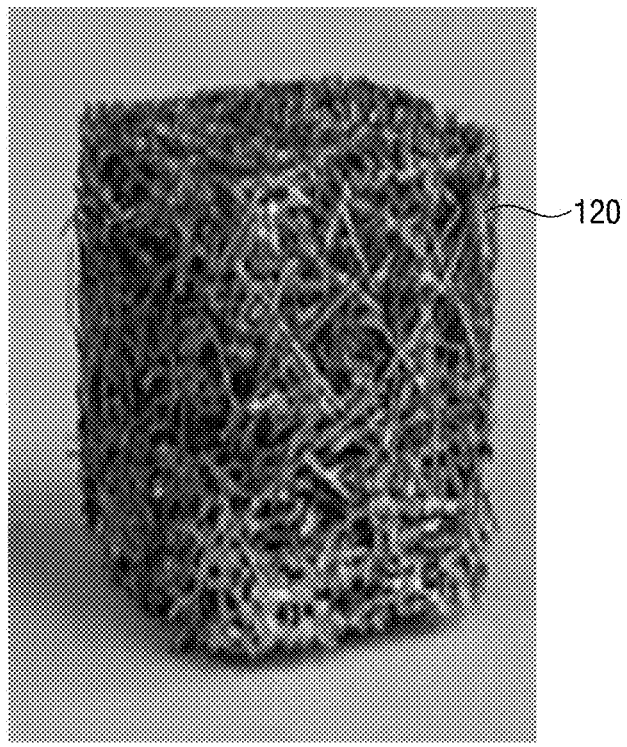
FIG. 2 is a diagram illustrating a scaffold according to an embodiment of the present invention.

FIG. 2 is a diagram illustrating a scaffold according to an embodiment of the present invention.

Referring to FIG. 2, a scaffold 120 is inserted into a bone damage site and serves as a support for bone cell regeneration. Here, the scaffold 120 refers to an artificially created structure for tissue establishment and cell function control. For example, the scaffold 120 may serve as a cell adhesion inducing substance and act as a support that bone cells are proliferated and differentiated.

Various ions required for bone cell regeneration are attached to the scaffold 120.
The ions required for bone cell regeneration may include a calcium ion, a phosphorous ion, various minerals, and the like.

The scaffold 120 is typically formed of a natural material and an artificial material. The natural material includes collagen, gelatin, chitin, chitosan, hyaluronic acid, and the like and the artificial material includes a ceramic material, a metal material, a polymer synthesis material, and the like. The polymer synthesis material includes polycaprolactone (PCL), polylactic-co-glycolic acid (PLGA), polylactic acid (PLA), polyglicolic acid (PGA), and the like.

Figure 3:
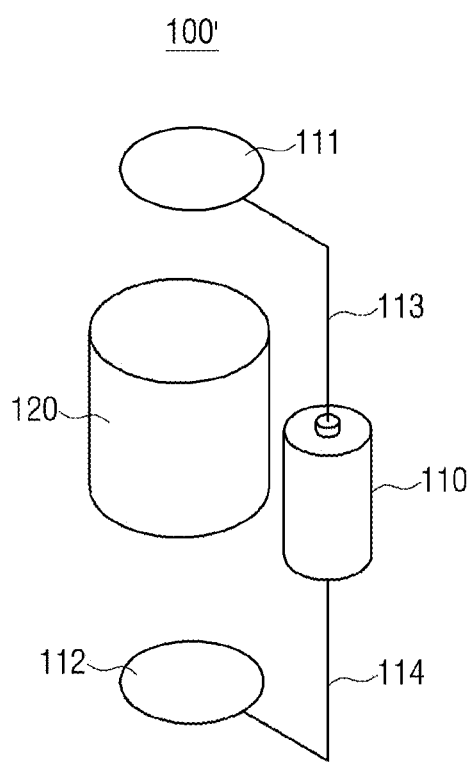
FIG. 3 is a diagram illustrating a bone regeneration device according to another embodiment of the present invention.

FIG. 3 is a diagram illustrating a bone regeneration device according to an embodiment of the present invention.

Referring to FIG. 3, a first electric conductor 111 is coupled to a first electrode of a battery 110 and is formed in one side of a scaffold 120. For example, the first electric conductor 111 may be formed in the one side of the scaffold 120 to be in contact with a surface of the scaffold 120 or to be spaced from the scaffold 120.

A second electric conductor 112 is coupled to a second electrode of the battery 110 and is formed in the other side of the scaffold 120. For example, the second electric conductor 112 may be formed in the other side of the scaffold 120, which is different from a direction in which the first electric conductor 111 is arranged, to be in contact with the surface of the scaffold 120 or to be spaced from the scaffold 120.

The battery 110 attracts the ions for bone cell regeneration by forming an electric field near the scaffold 120 through application of voltages to the first electric conductor 111 and the second electric conductor 112.

For example, in response to the voltages being applied to the first electric conductor 111 and the second electric conductor 112, a potential difference is generated between the first electric conductor 111 and the second electric conductor 112 and thus an electric field is formed between the first electric conductor 111 and the second electric conductor 112.

Calcium, phosphorous, and the like required for bone cell regeneration often exist in the body in an ionic form. Accordingly, in response to elements required for bone cell regeneration being negatively or positively charged as ions, the elements are trapped to the electric field formed between the first electric conductor 111 and the second electric conductor 112 and are moved. The scaffold 120 may be disposed between the first electric conductor and the second electric conductor and thus the ions may be attached to the scaffold 120. Accordingly, the bone cell regeneration may be promoted by disposing the scaffold 120 between the first electric conductor 111 and the second electric conductor 112.

The bone regeneration device 100 may include a switching circuit 115 configured to periodically change polarities of the first electric conductor 111 and the second electric conductor 112. For example, the switching circuit 115 may be coupled to the first electrode and the second electrode of the battery 110 and the first electric conductor 111 and the second electric conductor 112 and may periodically change the polarities of the first electric conductor 111 and the second electric conductor 112. For example, the switching circuit 115 may couple the first electrode and the first electric conductor 111 and couple the second electrode and the second electric conductor 112. In response to a fixed time being elapsed, the switching circuit 115 may couple the second electrode and the first electric conductor 111 and couple the first electrode and the second electric conductor 112. In response to the fixed time being elapsed again, the switching circuit 115 may couple the first electrode and the first electric conductor 111 and couple the second electrode and the second electric conductor 112. The bone regeneration device may prevent cations among the ions required for bone cell regeneration from being formed only in one-side direction and anions from being formed only in an opposite-side direction by periodically changing the polarities of the first electric conductor 111 and the second electric conductor 112 through the switching circuit 115.

For example, the first electric conductor 111 and the second electric conductor 112 may be disposed in directions opposite to each other with the scaffold interposed therebetween. In this example, a corresponding area between the first electric conductor 111 and the second electric conductor 112 may be increased and thus the intensity of the electric field formed between the first electric conductor 111 and the second electric conductor 112 may be increased.

It has been illustrated in FIG. 3 that the first electric conductor 111 and the second electric conductor 112 have the disc shape, but this is not limited thereto. For example, the first electric conductor 111 and the second electric conductor 112 may have a bone screw shape.

Figure 4A:
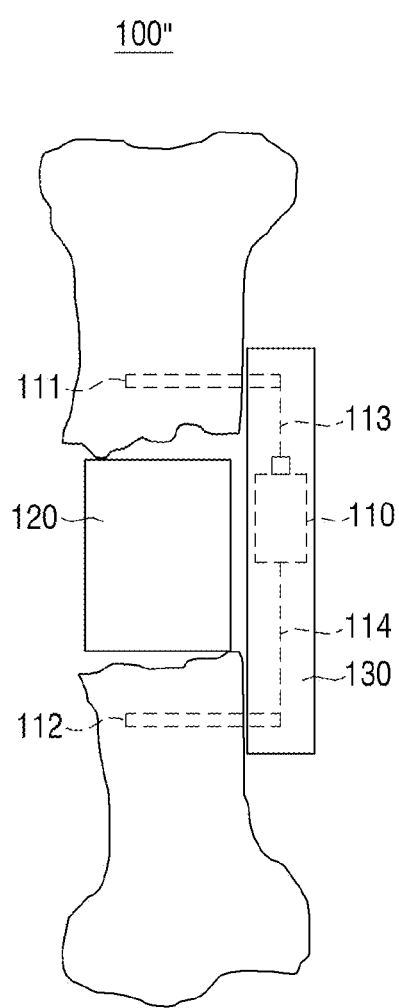
FIGS. 4A and 4B are diagrams illustrating bone regeneration devices according to another embodiment of the present invention.

FIG. 4A is a diagram illustrating a bone regeneration device according to an embodiment of the present invention.

Referring to FIG. 4A, a bone regeneration device 100" include a battery 110, a first electric conductor 111, a second electric conductor 112, a scaffold 120, and a support 130.

The first electric conductor 111 may be coupled to a first electrode of the battery 110 and may be inserted into a bone located in one side of the scaffold 120. One-end portion of the first electric conductor 111 may be coupled to the support 130 and the other-end portion of the first electric conductor 111 may be inserted into the bone so that the support 130 may fix the bone.

The second electric conductor 112 may be coupled to a second electrode of the battery 110 and may be inserted into a bone located in the other side of the scaffold 120. One-end portion of the second electric conductor 112 may be coupled to the support 130 and the other-end portion of the second electric conductor 112 may be inserted into the bone so that the support 130 may fix the bone.

The bone regeneration device 100" may include the support 130 on which the battery 120 is to be mounted. For example, the battery 110 may be inserted into the inside of the support 130. A first electric wiring 113 or a second electric wiring 114 may also be implemented in such a manner that the first electric wiring 113 or the second electric wiring 114 is inserted into the inside of the support 130. It has been described in the embodiment that the whole portion of the battery 110 is inserted into the inside of the support 130, but this is not limited thereto. For example, the battery 120 may be implemented in such a manner that a portion of the battery 120 may be inserted into the inside of the support 130 and a portion of the battery 120 may protrude from the outside of the support 130.

For example, the first electric conductor 111 and the second electric conductor 112 may be disposed in directions opposite to each other with the scaffold interposed therebetween. In this example, a corresponding area between the first electric conductor 111 and the second electric conductor 112 may be increased and thus the intensity of an electric field formed between the first electric conductor 111 and the second electric conductor 112 may be increased.

Figure 4B:
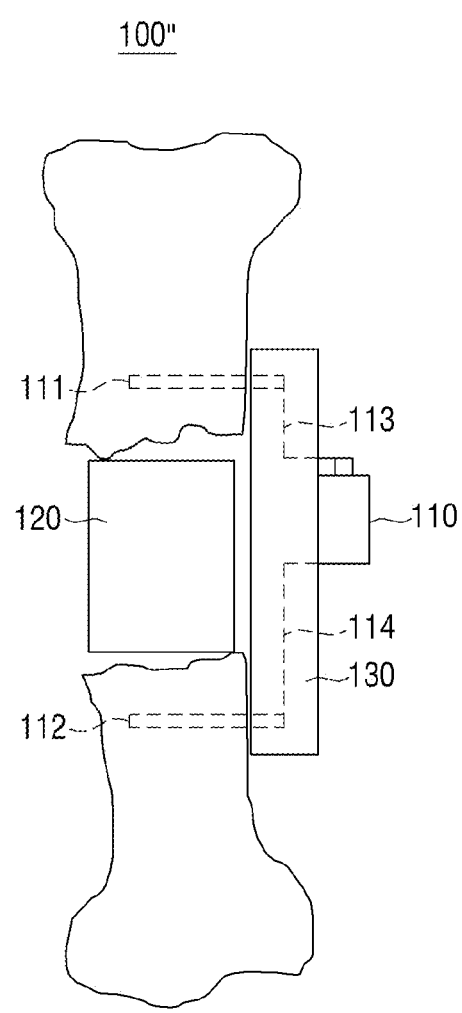

FIG. 4B is a diagram illustrating a bone regeneration device according to an embodiment of the present invention.

Referring to FIG. 4B, the battery 110 may be mounted on a surface of the support 130. The first electric wiring 113 may be inserted into the inside of the support 130 to couple the first electrode of the battery 110 to the first electric conductor 111. The second electric wiring 114 may be inserted into the inside of the support 130 to couple the second electrode of the battery 110 to the second electric conductor 112.

Figure 5A:
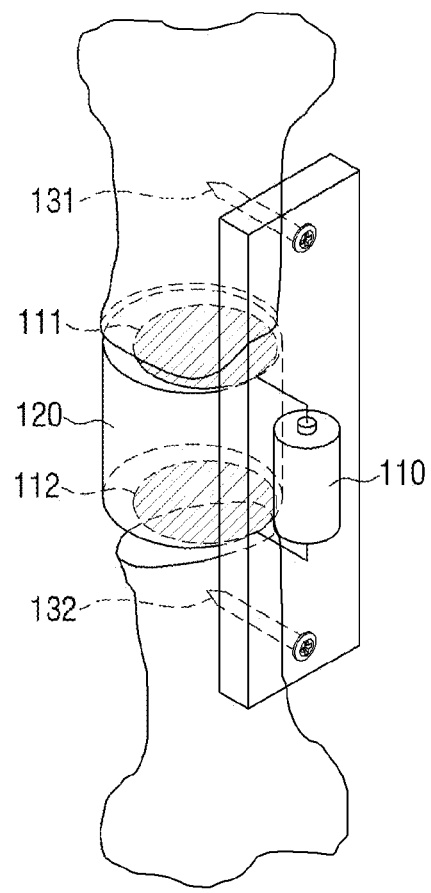
FIGS. 5A and 5B are diagrams three-dimensionally illustrating bone regeneration devices according to an embodiment of the present invention.

FIG. 5A is a diagram three-dimensionally illustrating a bone regeneration device according to an embodiment of the present invention.

A first fixing unit 131 and a second fixing unit 132 may be coupled to the support 130 and the first fixing unit 131 and the second fixing unit 132 may be inserted into bones around a bone damage site so that the support 130 may fix the bones around the bones damage site.

For example, the first fixing unit 131 and the second fixing unit 132 may be coupled to the support 130 and the first fixing unit 131 and the second fixing unit 132 may be inserted into the bones around the bone damage site. In this example, the first fixing unit 131 and the second fixing unit 132 may be fixed to the bones around the bone damage site so that the bones around the bone damage site apply pressure to the scaffold 120. Accordingly, the first fixing unit 131 and the second fixing unit 132 may fix the scaffold 120.

For example, as illustrated in FIG. 5A, the first electric conductor 111 and the second electric conductor 112 may be disposed in such a manner that the first electric conductor 111 and the second electric conductor 112 are in contact with the scaffold 120. In this example, since a distance between the first electric conductor 111 and the second electric conductor 112 is minimized, the intensity of the electric field formed between the first electric conductor 111 and the second electric conductor 112 may be increased.

It has been described in FIG. 5A that the first electric conductor 111 and the second electric conductor 112 are disposed to be in connect with the scaffold 120, but this is not limited thereto. For example, the first electric conductor 111 may be formed in an arbitrary point of one side of the scaffold 120. In this example, the first electric conductor 111 may be formed in the arbitrary point of the one side of the scaffold 120 even in such a manner that the first electric conductor is inserted into the bone.

For example, the second electric conductor 112 may be formed in an arbitrary point of the other side of the scaffold 120 which is different from a direction in which the first electric conductor 111 is disposed. In this example, the second electric conductor 112 may be formed in the arbitrary point of the other side of the scaffold 120 even in such a manner that the second electric conductor is inserted into the bone.

The first electric conductor 111 and the electric second conductor 112 may serve as a fixing unit separately from the first fixing unit 131 and the second fixing unit 132. For example, one-end portions of the first electric conductor 111 and the second electric conductor 112 may be coupled to the support 130 and the other-end portions of the first electric conductor 111 and the second electric conductor 112 may be inserted into the bone to serve as the fixing unit for fixing a bone.

It has illustrated in the embodiment that the support 130, the first fixing unit 131, and the second fixing unit 132 fix the bone divided into two, but this is not limited thereto. For example, the support 130 and the fixing units may fix a bone divided into three or more or may fix a bone which is not divided but is partially damaged. In this example, the bone regeneration device 100''' may be implemented to include three or more fixing units. A bone may be fixed through the support 130 and only one fixing unit.

It has been described in the embodiment that the scaffold 120 is separated from the support 130, but the bone regeneration device may be implemented in such a manner that the scaffold 120 is directly coupled to the support 130 and the scaffold 120 is fixed to the support 130.

Figure 5B:
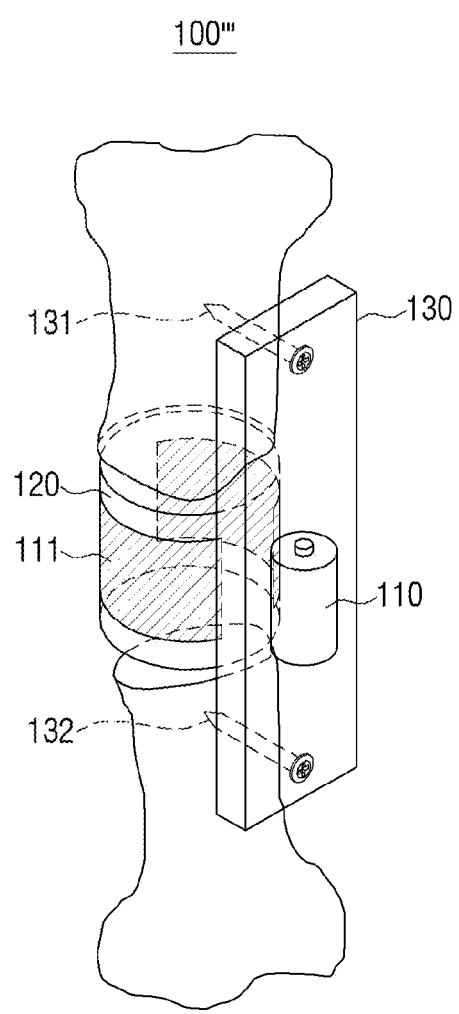

FIG. 5B is a diagram three-dimensionally illustrating a bone regeneration device according to an embodiment of the present invention.

It has been described in FIG. 5A that the first electric conductor 111 and the second electric conductor 112 are disposed in the directions in which the first fixing unit 131 and the second fixing unit 132 are located. However, referring to FIG. 5B, the first electric conductor 111 and the second electric conductor 112 may be disposed in arbitrary one side or the other side of the scaffold 120.

The first electric conductor 111 and the second electric conductor 112 may be coupled to the support 130 to be fixed to the support 130.

It has been described in the embodiment that the first electric conductor 111 and the second electric conductor 112 are disposed in directions opposite to each other with the scaffold 120 interposed therebetween, but this is not limited thereto. For example, in response to the first electric conductor 111 being disposed in a first direction from the scaffold 120, the second electric conductor 112 may be disposed not in the first direction but in an arbitrary direction from the scaffold 120.

Figure 6A:
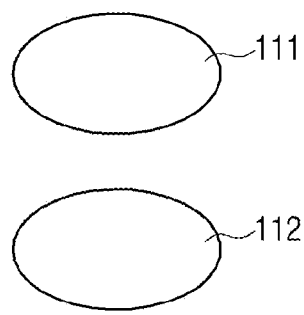
FIGS. 6A and 6B are diagrams illustrating a first electric conductor and a second electric conductor according to an embodiment of the present invention.
Figure 6B:
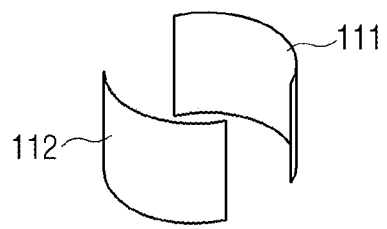

FIGS. 6A and 6B are diagrams illustrating first and second electric conductors according to an embodiment of the present invention.

Referring to FIG. 6A, the first electric conductor 111 and the second electric conductor 112 may have a plate shape.

As areas of the first electric conductor 111 and the second electric conductor 112 are increased, the intensity of the electric field formed between the first electric conductor 111 and the second electric conductor 112 is increased. To trap more ions, the first electric conductor 111 and the second electric conductor 112 may have a plate shape.

Referring to FIG. 6B, the first electric conductor 111 and the second electric conductor 112 may be implemented in such a manner that the first electric conductor 111 and the second electric conductor 112 are smoothly curved along a side of the scaffold to be attached to the side of the scaffold.

In addition to the first electric conductors 111 and the second electric conductors 112 illustrated in FIGS. 6A and 6B, the first electric conductor 111 and the second electric conductor 112 may have various shapes. For example, the first electric conductor 111 and the second electric conductor 112 may have a bone screw shape.

Figure 7:
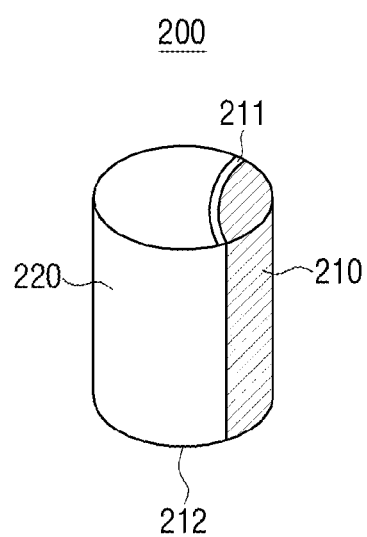
FIGS. 7 and 8 are diagrams illustrating bone regeneration devices according to another embodiment of the present invention.

FIG. 7 is a diagram illustrating a bone regeneration device according to another embodiment of the present invention.

Referring to FIG. 7, a bone regeneration device 200 includes a battery 210 and a scaffold 220.

The scaffold 220 is inserted into a bone damage site and serves as a support so that bone cells may be regenerated. Here, the scaffold 220 refers to an artificially created structure for tissue establishment and cell function control. For example, the scaffold 220 may serve as a cell adhesion inducing substance and act as a support that bone cells are proliferated and differentiated.

The battery 210 is disposed in the scaffold 220. It has been illustrated in FIG. 7 that the battery 210 is disposed in a surface of the scaffold 220. However, the battery may be implemented even in such a manner that the battery is inserted into the inside of the scaffold 220.

The battery 210 may be attached and fixed to the scaffold 220 in a form which surrounds the scaffold 220.

A first electrode 211 of the battery 210 is formed in one side of the scaffold 220. For example, the first electrode 211 may be disposed in the one side of the scaffold 220 to be in contact with the surface of the scaffold 220 or to be spaced from the scaffold 220.

A second electrode 212 of the battery 210 is formed in the other side of the scaffold 220. For example, the second electrode 212 may be formed in the other side of the scaffold 220, which is different from a direction in which the first electrode 211 is disposed, to be in contact with the surface of the scaffold 220 or to be spaced from the scaffold 220.

The battery 210 attracts the ions for bone cell regeneration by forming an electric field between the first electrode 211 and the second electrode 212 through application of voltages to the first electrode 211 and the second electrode 212.

For example, in response to the voltages being applied to the first electrode 211 and the second electrode 212, a potential difference between the first electrode 211 and the second electrode 212 is generated and thus an electric field is formed between the first electrode 211 and the second electrode 212.

For example, calcium, phosphorous, and the like required for bone cell regeneration may often exist in the body in an ionic form. Accordingly, in response to elements required for bone cell regeneration being negatively or positively charged as ions, the elements are trapped to the electric field formed between the first electrode 211 and the second electrode 212 and are moved. In this example, the scaffold 220 may be disposed between the first electrode 211 and the second electrode 212 and thus the ions may be attached to the scaffold 220. Accordingly, the bone cell regeneration may be promoted by disposing the scaffold 220 between the first electrode 211 and the second electrode 212.

The first electrode 211 and the second electrode 212 may be formed in directions opposite to each other toward the scaffold 220. For example, the outside of the battery 210 may be formed of an insulator. In this example, the first electrode 211 and the second electrode 212 may be formed between the insulator in the outside of the battery 210 and the scaffold 220. Accordingly, the first electrode 211 and the second electrode 212 may be formed toward the scaffold 220.

For example, the first electrode 211 and the second electrode 212 may be formed in parallel in the directions opposite to each other with the scaffold 220 interposed therebetween. In this example, a corresponding area between the first electrode 211 and the second electrode 212 may be increased and thus the intensity of an electric field formed between the first electrode 211 and the second electrode 212 may be increased.

For example, the bone regeneration device 200 may further include a first electric conductor (not shown) coupled to the first electrode 211 and a second electric conductor (not shown) coupled to the second electrode 212. In this example, the first electric conductor (not shown) and the second electric conductor (not shown) may be disposed in one side and the other side of the scaffold 220 to form an electric field on the scaffold.

The bone regeneration device 200 may include a switching circuit (not shown) configured to periodically change polarities of the first electric conductor (not shown) and the second electric conductor (not shown). For example, the switching circuit (not shown) may be coupled to the first electrode 211 and the second electrode 212 of the battery 210 and the first electric conductor (not shown) and the second electric conductor (not shown) and periodically change the polarities of the first electric conductor (not shown) and the second electric conductor (not shown). In this example, the switching circuit may couple the first electrode 211 and the first electric conductor (not shown) and couple the second electrode 212 and the second electric conductor (not shown). Then, in response to a fixed time being elapsed, the switching circuit may couple the second electrode 212 and the first electric conductor (not shown) and couple the first electrode 211 and the second electric conductor (not shown). In response to the fixed time being elapsed again, the switching circuit may couple the first electrode 211 and the first electric conductor (not shown) and couple the second electrode 212 and the second electric conductor (not shown). The bone regeneration device may prevent cations and anions among the ions required for bone cell generation from being formed only in one-side direction and only in an opposite-side direction by periodically changing the polarities of the first electric conductor (not shown) and the second electric conductor (not shown) through the switching circuit.

The outside of the battery 210 may be formed of a biocompatible material and may prevent the human body from being harmful.

Figure 8:
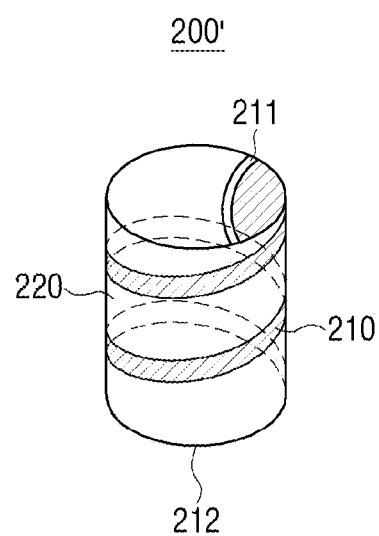

FIG. 8 is a diagram illustrating a bone regeneration device according to another embodiment of the present invention.

Referring to FIG. 8, a battery 210 may be a variable battery which surrounds the scaffold. Here, the variable battery may refer to a battery of which a shape is freely deformed. For example, the variable battery may have a thread shape. Here, the thread-shaped battery has various shapes such as a cylindrical shape or a rectangular parallelepiped shape and the thread shape refers to a bendable or twistable shape in which a length thereof is significantly large as compared with a cross-section area thereof.

As illustrated in FIG. 8, the battery 210 may be a thread-shaped variable battery and may have a shape which surrounds the scaffold 220. However, this is not limited thereto and the battery 210 may be implemented to have various forms.

Figure 9:
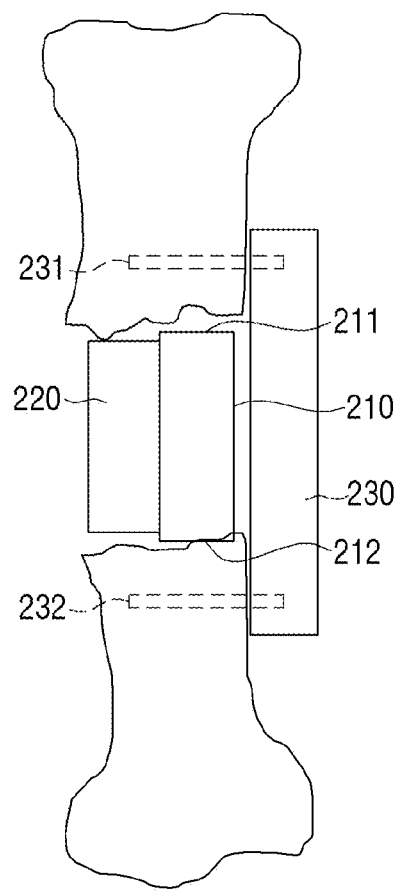
FIG. 9 is a diagram illustrating a bone regeneration device according to another embodiment of the present invention.

FIG. 9 is a front view illustrating a bone regeneration device according to an embodiment of the present invention.

Referring to FIG. 9, a bone regeneration device including a scaffold 220 and a battery 210 may be used together with a support 230 and fixing units 231 and 232.

The support 230 may be coupled to a first fixing unit 231 and a second fixing unit 232 and the first fixing unit 231 and the second fixing unit 232 may be inserted into bones near a bone damage site so that the support 230 may fix the bones.

The support 230 may be coupled to the first fixing unit 231 and the second fixing unit 232 and the first fixing unit 231 and the second fixing unit 232 may be inserted into the bones near the bone damage site. The bones near the bone damage site may be fixed through the first fixing unit 231 and the second fixing unit 232 to apply pressure to the scaffold 220 and thus the scaffold 220 may be fixed.

It has been described in the embodiment that the scaffold 220 is separated from the support 230, but the bone regeneration device may be implemented in such a manner that the scaffold 220 is directly coupled to the support 230 and the scaffold 220 is fixed to the support 230.

Figure 10:
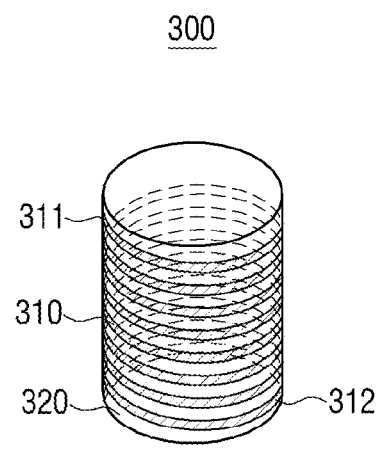
FIG. 10 is a diagram illustrating a bone regeneration device which forms a magnetic field in main surface of a scaffold according to an embodiment of the present invention.

FIG. 10 is a diagram illustrating a bone regeneration device which forms a magnetic field in a main surface of a scaffold according to an embodiment of the present invention.

Referring to FIG. 10, a bone regeneration device 300 includes a battery 310 and a scaffold 320.

The battery 310 is a thread-shaped variable battery which surrounds the scaffold 320. Here, the variable battery refers to a battery of which a shape is freely deformed. For example, the variable battery may have a thread shape. Here, the thread-shaped battery has various shapes such as a cylindrical shape or a rectangular parallelepiped shape and the thread shape refers to a bendable or twistable shape in which a length thereof is significantly large as compared with a cross-section area thereof.

A first electrode 311 and a second electrode 312 of the battery 310 are electrically coupled to each other.

The first electrode 311 and the second electrode 312 of the battery 310 may be electrically coupled to each other and thus a magnetic field may be formed around the scaffold 320.

Calcium, phosphorous, and the like required for bone cell regeneration often exist in the body in an ionic form. Accordingly, in response to elements required for bone cell regeneration being negatively or positively charged as ions, the elements are trapped to the magnetic field formed around the scaffold 320 and are moved. The ions may be attached to the scaffold 320 and the bone cell regeneration may be promoted.

Current may flow in the inside of the battery 310. For example, the thread-shaped battery may include a current collector (not shown) together with an electrolyte. In this example, the current collector (not shown) may also have a thread shape and may be coupled from the first electrode 311 to the second electrode 312 in the inside of the battery 310. In response to the first electrode 311 and the second electrode 312 being electrically coupled, the current may flow through the current collector (not shown) in the inside of the battery 310 and thus the magnetic field may be formed around the scaffold 320.

The outside of the battery 210 may be formed of a biocompatible material and may prevent the human body from being harmful.

The foregoing exemplary embodiments and advantages are merely exemplary and are not to be construed as limiting the present inventive concept. The description of the exemplary embodiments is intended to be illustrative, and not to limit the scope of the claims, and many alternatives, modifications, and variations will be apparent to those skilled in the art.

The invention claimed is:

1. A bone regeneration device which forms an electric field on a scaffold inserted into a bone damage site, the bone regeneration device comprising:
   a battery;
   a first electric conductor which is coupled to a first electrode of the battery and is to be inserted into a bone located in one side of the scaffold; and
   a second electric conductor which is coupled to a second electrode of the battery and is to be inserted into a bone located in the other side of the scaffold,
   wherein the battery applies a voltage to the first electric conductor and the second electric conductor to form an electric field between the first electric conductor and the second electric conductor, and
   wherein the scaffold is located between the first electric conductor and the second electric conductor, and ions for bone cell generation are attached by the electric field formed between the first electric conductor and the second electric conductor.

2. The bone regeneration device according to claim 1, further comprising a support on which the battery is to be mounted,
   wherein one-end portions of the first electric conductor and the second electric conductor are coupled to the support and the other-end portions of the first electric conductor and the second electric conductor are inserted into bones.

3. The bone regeneration device according to claim 1, wherein the first electric conductor and the second electric conductor have a plate shape.

4. The bone regeneration device according to claim 1, further comprising a switching circuit configured to periodically change polarities of the first electric conductor and the second electric conductor.

5. A bone regeneration device, comprising:
   a battery having a first electrode and a second electrode;
   a scaffold insertable into a bone at a damage site so as to serve as a support for bone cell regeneration;
   a first electric conductor coupled to the first electrode, the first electric conductor being insertable into the bone at one side of the damage site; and
   a second electric conductor coupled to the second electrode, the second electric conductor being insertable into the bone at an opposite side of the damage site,
   wherein the battery applies voltage to the first electric conductor and the second electric conductor so as to form an electric field across the damage site between the first electric conductor and the second electric conductor.

6. The bone regeneration device according to claim 5, further comprising a support on which the battery is to be mounted,
   wherein the first electric conductor and the second electric conductor have first end portions coupled to the support, and wherein the first electric conductor and the second electric conductor have second end portions that are insertable into the bone.

7. The bone regeneration device according to claim 5, wherein the first electric conductor and the second electric conductor have a plate shape.

8. The bone regeneration device according to claim 5, further comprising a switching circuit configured to periodically change polarities of the first electric conductor and the second electric conductor.

* * * * *